United States Patent
Asay et al.

(10) Patent No.: US 6,465,255 B1
(45) Date of Patent: Oct. 15, 2002

(54) METHOD FOR IDENTIFYING AND PROBING PHASE TRANSITIONS IN MATERIALS

(75) Inventors: Blaine W. Asay; Bryan F. Henson; Robert K. Sander; Jeanne M. Robinson; Steven F. Son; Peter M. Dickson, all of Los Alamos, NM (US)

(73) Assignee: The Regents of the University of California, Los Alamos, NM (US)

(*) Notice: Subject to any disclaimer, the term of this patent is extended or adjusted under 35 U.S.C. 154(b) by 0 days.

(21) Appl. No.: 09/493,645

(22) Filed: Jan. 28, 2000

Related U.S. Application Data
(60) Provisional application No. 60/117,900, filed on Jan. 29, 1999.

(51) Int. Cl.$^7$ ............................................... G01N 21/75
(52) U.S. Cl. ........................... 436/164; 436/4; 252/582; 356/30; 356/446
(58) Field of Search ..................... 436/164, 4; 252/582; 356/30, 446

(56) References Cited

U.S. PATENT DOCUMENTS

| | | | | |
|---|---|---|---|---|
| 3,820,087 A | * | 6/1974 | Chaudhari et al. | 340/173 |
| 4,975,358 A | * | 12/1990 | Connenschein et al. | 430/495 |
| 5,623,341 A | * | 4/1997 | Hunt | 356/300 |
| 6,207,178 B1 | * | 3/2001 | Westesen et al. | 424/405 |

OTHER PUBLICATIONS

S. F. Son, B. W. Asay, B. F. Henson, R. K. Sander, A. N. Ali, P. M. Zielinski, D. S. Phillips, R. B. Schwarz, and C. B. Skidmore, "Dynamic Observation of a Thermally Activated Structure Change in 1,3,5–Triamino–2,4,6–trinitrobenzene (TATB) by Second Harmonic Generation," J. Phys. Chem. B. vol. 103, No. 26, pp. 5434–5440, Jun. 1999.

R. J. Karpowicz, L. S. Gelfand, and T. B. Brill, "Applicability of Solid–Phase Transition Kinetics to the Properties of HMX," AIAA Journal, vol. 21, No. 2, pp. 310–312, May 1982.

B. F. Henson, K. R. Wilson, and J. M. Robinson, "Quantitative Measurements of Multilayer Physical Adsorption on Heterogeneous Surfaces from Nonlinear Light Scattering," Physical Review Letters, vol. 79, No. 8, pp. 1531–1534, Aug. 1997.

D. J. LeCaptain and K. A. Berglund, "The Application of Second Harmonic Generation for In situ Measurement of Induction Time of Selected Crystallization Systems," Journal of Crystal Growth 203, pp. 564–569, 1999.

R. Cameroni, M. T. Bernabei, F. Forni, G. Coppi, "Polymorphism of Chloramphenicol Stearate," Farmaco Edizione Pratica, vol. 33, fasc. 10, pp. 447–454, 1978.

Israel Goldberg and Yigal Becker, "Polymorphs of Tamoxifen Citrate: Detailed Structural Characterization of the Stable Form," Journal of Pharmaceutical Sciences, vol. 76, No. 3, pp. 259–264, Mar. 1987.

* cited by examiner

*Primary Examiner*—Jill Warden
*Assistant Examiner*—Monique T. Cole
(74) *Attorney, Agent, or Firm*—Samuel L. Borkowsky

(57) ABSTRACT

The present invention includes a method for identifying and probing phase transitions in materials. A polymorphic material capable of existing in at least one non-centrosymmetric phase is interrogated with a beam of laser light at a chosen wavelength and frequency. A phase transition is induced in the material while it is interrogated. The intensity of light scattered by the material and having a wavelength equal to one half the wavelength of the interrogating laser light is detected. If the phase transition results in the production of a non-centrosymmetric phase, the intensity of this scattered light increases; if the phase transition results in the disappearance of a non-centrosymmetric phase, the intensity of this scattered light decreases.

5 Claims, 3 Drawing Sheets

METHOD FOR IDENTIFYING AND PROBING PHASE TRANSITIONS IN MATERIALS

RELATED APPLICATIONS

This application claims the benefit of U.S. Provisional Application No. 60/117,900 filed on Jan. 29, 1999, which is herebyincorporated by reference.

This invention was made with government support under Contract No. W-7405-ENG-36 awarded by the U.S. Department of Energy to The Regents of the University of California. The U.S. government has certain rights in the invention.

FIELD OF THE INVENTION

The present invention relates generally to monitoring phase transitions in materials and, more particularly, to a method for using second harmonic generation (SHG) to identify and probe phase transitions in polymorphic materials.

BACKGROUND OF THE INVENTION

By providing the appropriate thermal or mechanical input, phase transitions may be induced in materials. Phase transitions are generally identified by monitoring changes in a physical property or properties of the material during thermal and/or mechanical input. The elucidation of the phase transition behavior a material is important in understanding the properties of the material. Thus, the development of methods for identifying and probing phase transitions in materials is of great interest.

Many materials, such as organic and inorganic compounds and polymers, exhibit polymorphism; they can exist in more than one crystallographically distinct crystalline phase. These crystalline phases, known as polymorphs, can be centrosymmetric phases that have inversion symmetry, or non-centrosymmetric crystalline phases that do not have inversion symmetry. Although the individual polymorphs of a polymorphic material have the same chemical composition, they can have significantly different physical properties. For example, four distinct crystalline phases have been identified for the energetic organic compound octahydro-1,3,5,7-tetranitro-1,3,5,7-tetrazocine (HMX). While the beta phase of HMX (β-HMX) is relatively insensitive to changes in temperature and pressure, explosive decomposition may be induced in the delta phase of HMX (δ-HMX) with thermal and/or shock input.

Many important biologically active compounds exhibiting pharmaceutical activity, herein referred to as pharmaceuticals, are polymorphic; these include the antidiabetic drug tolbutamide, the antibiotic chloramphenicol, and the selective estrogen response modulator tamoxifen. The phase behavior and physical properties of polymorphic pharmaceuticals must be thoroughly understood, since the properties of the various polymorphs of a pharmaceutical may different. For example, individual polymorphs of a polymorphic pharmaceutical can exhibit different rates of dissolution, which can affect their concentration in body tissues and therefore their effectiveness.

The development of crystallization procedures to induce the formation of a desired polymorph is usually expensive and time consuming. Optimizing these procedures usually involves determining operating temperatures, operating pressures, rates of heating or cooling, solvents, concentrations of materials, and other parameters. Rapid non-invasive, in-situ dynamic monitoring during crystallization can provide important information regarding the formation of desired and undesired polymorphs of polymorphic materials. While Raman spectroscopy has been used for the detection of polymorphic transitions, system costs are prohibitively expensive at the laboratory scale, and will likely limit use on the industrial scale.

It is extremely important to understand the phase behavior of polymorphic materials. Clearly, a rapid and sensitive method for identifying and probing the phase transitions of polymorphic materials is highly desirable.

Therefore, an object of the present invention is a rapid and highly sensitive method for identifying and probing phase transitions of polymorphic materials.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the invention includes a method for identifying and probing phase transitions in materials. A polymorphic material capable of existing in at least one non-centrosymmetric phase is interrogated by a beam of laser light at a chosen wavelength and frequency. A phase transition is induced in the material whilst it is interrogated. The intensity of light scattered by the material and having a wavelength equal to one half the wavelength of the interrogating laser light is detected. If the phase transition results in the production of a noncentrosymmetric phase, the intensity of this scattered light increases. If the phase transition results in the disappearance of a non-centrosymmetric phase, the intensity of this scattered light decreases.

BRIEF DESCRIPTION OF THE DRAWINGS

The accompanying drawings, which are incorporated in and form a part of the specification, illustrate embodiments of the present invention and, together with the description, serve to explain the principles of the invention.

In the Figures.

DETAILED DESCRIPTION OF THE INVENTION

Figure 1:
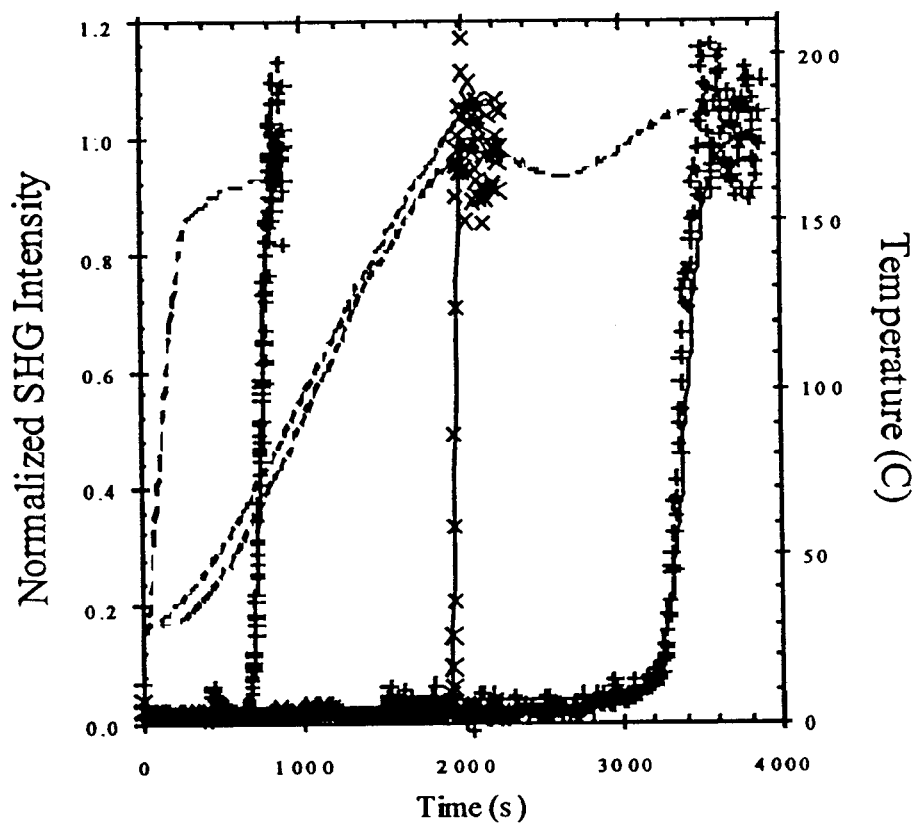
FIG. 1 is a graphical representation of a heating curve for HMX showing changes in SHG intensity and temperature versus time.

Reference will now be made in detail to the present preferred embodiments of the invention, examples of which are illustrated in the accompanying drawings. Similar or identical structure is identified using identical callouts.

The present invention includes a method that uses a pulsed coherent laser beam to probe rapidly a material in order to determine its crystalline phase. A polymorphic material is interrogated by a pulsed laser beam, and scattered light at half the wavelength (twice the frequency) of the input beam is detected and measured. This scattered light arises from a non-linear optical process known as second harmonic generation (SHG), which occurs when high-intensity laser light interacts with a non-centrosymmetric crystalline lattice.

The method does not require any particular sample preparation procedure. The method is a zero background method and therefore highly sensitive, since any non-crystalline or centrosymmetric crystalline background material does not contribute to the SHG signal. The method is also rapid; it can make temporally resolved measurements on time scales of picoseconds and spatially resolved measurements in the micron range.

The method can be used to detect the appearance or disappearance of the noncentrosymmetric phase during the phase transition. The method can be used to detect the appearance or disappearance of a non-centrosymmetric phase in solid-solid transitions and in liquid-solid transitions. For example, crystallization of a polymorphic material originally in the liquid phase or dissolved in a solvent can be detected with the method of the present invention.

Materials that can be used with the method include organic and inorganic compounds, polymers, and mixtures thereof. For example, a polymorphic organic compound capable of existing in a non-centrosymmetric phase to provide a detectable SHG signal can be used. The method was demonstrated, as described in detail below, by identifying the beta-delta phase transition in HMX and measuring the kinetics of this transition.

HMX exhibits a wide variety of behaviors when subjected to various thermal fields. Temperatures just above 450° C. induce explosion after an induction time of $10^5$–$10^1$ seconds (s). IR laser irradiation generates surface temperatures from 500–700 K. and ignition at $10^{-3}$–$10^1$ s. Shear or frictional heating of pressed solids to 700–900 K. results in ignition in $10^{-4}$ s. Planar shocks from 10 GPa result in detonation over a time of about $10^{-7}$–$10^{-6}$ s.

It has been recognized for 30 years that the crystalline phases of HMX may play a role in the decomposition chemistry. Of the four phases of HMX identified, two have been of traditional concern, β-HMX, a low temperature form, and δ-HMX, a high temperature form that is the only phase observed upon low pressure heating of all four polymorphs. Differences in burn rate and drop-height sensitivity are known for the β- and δ- phases, with δ-HMX the more hazardous material. Kinetic measurements of the β-δ transition have shown that the first order activation energy and frequency factor resemble those attributed to chemical decomposition, supporting previous speculation that the initial decomposition step in HMX is coupled to, or preceded by, the formation of δ-HMX.

No in-situ measurements of the rate of the transformation have been reported for ignition experiments. Identification of the phase and transition rate have relied on traditional calorimetry, Fourier Transform Infrared Spectroscopy (FT-IR), and Raman techniques addressing times and temperatures of $10^2$–$10^5$ s and 450–500 K. However, the role of the β-δ transition during ignition has remained uncertain, and the validity of extrapolating measured transition rates to ignition times of less than a second has not been established.

The method of the present invention was first used to monitor the β-δ transition during slow heating to verify that temperatures and times are consistent with established kinetics. The method was then used to identify the β-δ transition during a dynamic ignition experiment. The β-δ transition was observed at the surface of a pressed polycrystalline sample during laser irradiation at a wavelength of about 10.6 $\mu$m (20 Watts/cm$^2$-s) prior to ignition. The transition time and surface temperature were consistent with low temperature measurements, validating the extrapolation of calculated transition rates to times of $10^{-2}$ s.

SHG was observed both in transmission through a thin layer of powdered crystal and in reflection from the surface of a pressed polycrystalline pellet. The relative SHG cross sections from β-HMX and δ-HMX were measured, and the phase transition was observed during slow heating. Powdered crystalline samples of a $KH_2PO_4$ (KDP) standard, and β- or δ-HMX (1–500 $\mu$m diameter) were mounted as thin layers of powder (about 500 $\mu$m thick) between sapphire windows. This cell was enclosed in an oven and placed in the optical path of a 10 Hz Nd:YAG laser light beam delivering 10 nanosecond (ns) pulses at 1064 nanometers (nm), (10–100 MW/cm$^2$). Diffuse forward-scattered SHG light was filtered to remove the 1064 nm fundamental light, focused into a monochrometer, and detected with a photo-tube. The scattered intensity followed the square of the input intensity, with no strong dependence on input or detection polarization. The spectra of SHG from the δ-HMX so and KDP were centered at 532 nm and consistent with the elastic conversion of the 1064 nm input pulse to 532 nm. Illumination of KDP samples with an intensity of 24 MW/cm$^2$ led to generation of 532 nm consistent with the large KDP cross section. By contrast, the SHG from δ-HMX was lower by a factor of 50 relative to δ-HMX. This is consistent with the crystallographic symmetry of the two polymorphs, with β-HMX a centrosymmetric, monoclinic structure of P2$_1$/c space group, and δ-HMX a non-centrosymmetric, hexagonal structure of space group P6$_1$22. Thus, SHG in the ⊕ polymorph should [thus] be strongly suppressed relative to the δ polymorph due to symmetry considerations, and this is what is observed. Additionally, the two polymorphs differ in several other respects, with a 7% volume expansion on transformation from the β polymorph to the δ polymorph and a change in unit cell participation from 2 molecules in the beta polymorph to 6 in the 8 polymorph. Also, the very polar nitro groups are nearly trans in the p polymorph and cis in the δ polymorph, leading to a significant change in dipole moment and reduction of molecular point group symmetry upon transition. For applications to thermal decomposition in energetic materials, this difference in cross-section for β-HMX and δ-HMX provides excellent contrast for use as an in-situ probe in dynamic experiments. This is a non-resonant application of SHG and therefore does not provide spectroscopic identification of any specific HMX phase. The contrast in cross-section between the β- and δ-HMX polymorphs allows the use of the SHG intensity to measure the rate of transformation between them where the initial and product phases of HMX have already been identified.

FIG. 1 shows a graphical representation of data obtained from slow heating of three samples of β-HMX. The data are plotted as the SHG intensity (symbols) normalized to maximum signal on the left axis, and the temperature (dashed lines) on the right axis, both as a function of time. The transition to δ-HMX is apparent as a rapid increase in the SHG, occurring at temperatures of about 170° C. If one considers the normalized SHG intensity, varying from 0–1, as proportional to the δ-HMX mole fraction, these data may be modeled using the kinetic first order rate law below:

$$dc/dt = k(\beta_0 - c)(\delta_0 + c)$$

The above equation is first order in both β and δ; c is the concentration of δ formed, $\beta_0$ and $\delta_0$ are the initial concentrations of β-HMX and δ-HMX respectively, t is the time and k is an Arrhenius rate expression, $k = A \times EXP(-E_a/RT)$. The partially integrated rate law, normalized to $\beta_0$, is $$x(T, t) = \frac{f\,EXP\left[\beta_0 \int_0^t k(T, t)dt\right]}{f\,EXP[\beta_0 \int_0^t k(T, t)dt] + 1}$$

where x is the fraction of β-HMX converted to δ, and f is the initial ratio of δ to β, $\cdot_0/\beta_0$. The normalized SHG intensity can then be expressed as a function of the δ-HMX fraction and a constant, e, which is the ratio of SHG intensity from pure β- and δ-HMX, shown below:

$$\frac{I_{2\omega}}{I_{2\omega}^{max}} = [e(1+x) + x]^2$$

The solid lines in FIG. 1 for each curve were calculated with these formulae, utilizing $E_a$, A, and f as fitting parameters. The optimized parameters were $E_a$=201.6(2.0) kJ/mol, log(A)=21.9(0.8), A in cm$^3$/g-s, and log(f)=−2.6(1.0), with the standard deviation at 95% confidence in parenthesis. Others have observed approximate first order behavior for the transition at low levels of conversion and determined the Arrhenius parameters to be Ea=204(2.0) kJ/mol, log(A)= 19.9(1.0) 1/s, with uncertainty in parenthesis. Observation of complete conversion leads to the use of a second order rate law. Our observations are consistent with what others have observed, and serve to quantify the observed SHG as a kinetic probe, yielding Arrhenius parameters consistent with those observed previously, and the assignment of a second order HMX rate law to the process. In addition, although kinetic measurements have been performed for all four phases of HMX, δ-HMX was the only product observed during heating at low pressure. We rely on these and subsequent observations to assign the transition observed here to the β-δ HMX transition.

Figure 2:
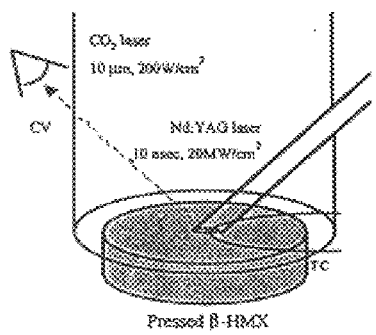
FIG. 2 is a schematic representation of the configuration used for the laser ignition of HMX.
Figure 3:
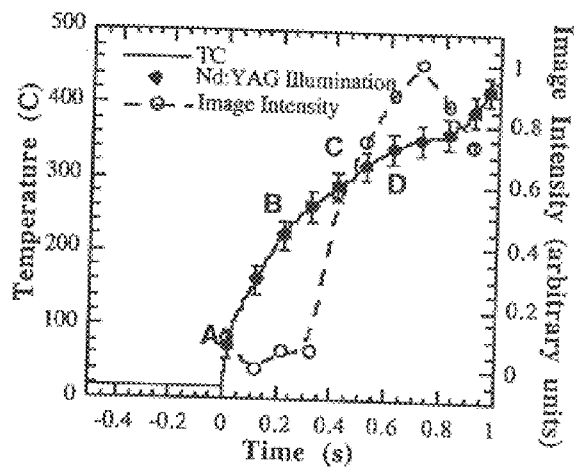
FIG. 3 is a graphical representation of the average image intensity and the temperature as a function of time relating to the laser ignition of HMX.
Figure 4:
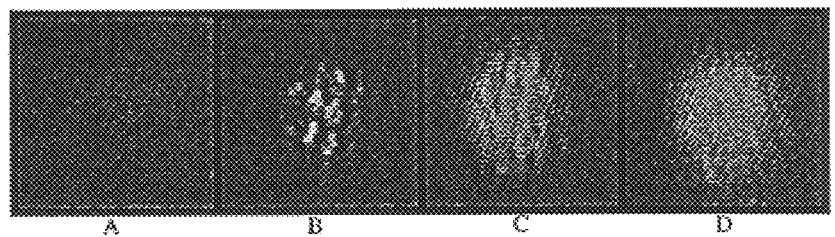
FIG. 4 shows selected SHG images during the β-δ HMX transition.

The configuration used for the laser ignition of HMX is shown in FIG. 2. A pressed pellet of HMX is illuminated by the continuous output of a $CO_2$ laser at a wavelength of about 10.6 μm. Interference effects from beam integration result in a cross-hatched pattern of slight surface temperature variability. A laser beam from a 10 Hz Nd:YAG laser, identical to the previous description, was directed onto the surface at an angle of about 30 degrees from normal, and a color video camera was used to image the SHG light at the surface along the specular reflection axis of the 1064 nm illumination. A 13 μm diameter thermocouple (type K), centered at the 1064 nm illumination spot on the surface, was used to record the temperature during heating. The $CO_2$ illumination was begun at time $t=t_0$, and the temperature rise was monitored until ignition in the gas phase approximately one second later. During heating, the SHG emission from the surface was imaged at the video rate of 60 Hz. A graphical representation of the temperature and the average image intensity as a function of time is shown in FIG. 3. Selected images of SHG appearance are shown FIG. 4. FIG. 3 shows the temperature recorded by the thermocouple as a function of time. The letters [shown] along the curve in FIG. 3 correspond to those below selected images in FIG. 4 and indicate the time and temperature at which the images of FIG. 4 were recorded. The images are from the video record of the 1064 nm illumination spot. SHG light first appears at approximately 250 milliseconds (ms), with an uncertainty from the framing rate of 30 ms, and clearly reflects the cross-hatched heating pattern on the surface. The appearance of the SHG light indicates the transition from β-HMX to δ-HMX at the surface and from the average intensity of the video image. The transition time is determined to be 366(100) ms at a homogeneous surface temperature of 277(30)° C.

Figure 5:
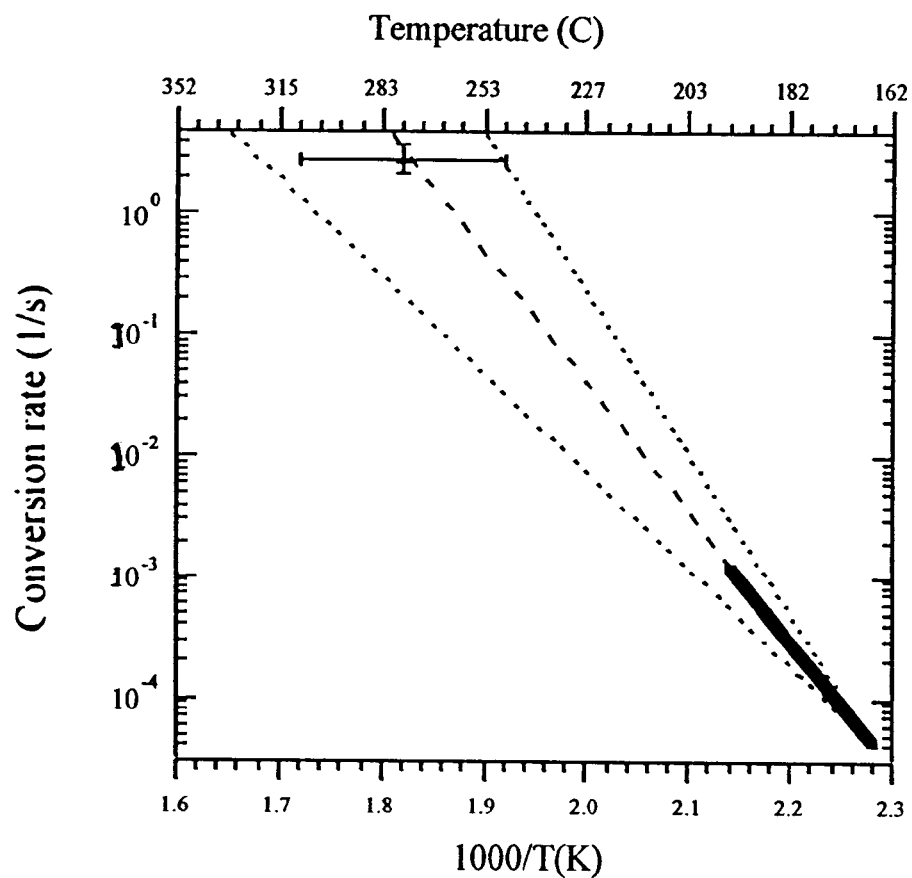
FIG. 5 is an Arrhenius plot of the observed β-δ HMX transition kinetics.

An Arrhenius plot of the observed β-δ transition kinetics is shown in FIG. 5. The solid bar is an average of data observed by others. The dashed lines reflect the uncertainties in rate at higher temperatures that result from extrapolation of data with the reported uncertainties. The data that results from this work are plotted as the inverse of the time to transition as a function of inverse temperature and are clearly consistent with the low temperature measurements. This verifies the extrapolation of these kinetics to combustion regimes that were first discussed many years ago. To our knowledge, the method of the present invention has provided the first measurements of a crystalline phase during a dynamic ignition.

The method was used similarly to probe phase transitions in other polymorphic organic compounds, including 1,3,5-triamino-2,4,6-trinitrobenzene (TATB) and 2,4,6,8,10,12-hexanitro-2,4,5,8,10,12-hexaazatetracyclo[5.5.0.0.$^{5,9}$0.$^{3,11}$] dodecane. Obviously, the method can be used to identify and probe phase transitions in other polymorphic crystals having at least one non-centrosymmetric phase capable of second harmonic generation upon interrogation with a laser light beam. For example, the invention can be used to identify and probe phase transition behavior in polymorphic materials such as in organic compounds having pharmaceutical activity, in inorganic compounds, and in polymers. The invention can also be used to provide kinetic information, such as the rates of transition of one polymorph to another. The invention can be used to identify and probe phase transtions during the crystallization of polymorphic pharmaceuticals to monitor the production of non-centrosymmetric crystalline phases during the crystallization process. Crystallizations may include crystallizations from solid powders, from liquid phases of polymorphic materials, and from solutions of the dissolved polymorphic materials. Crystallization from solution can involve dissolving a polymorphic solid in a solvent and crystallizing a desired polymorph from the solution by lowering the temperature of the solution, by removing solvent, by adding a crystallizing agent such as a co-solvent, etc. The solution is interrogated with a laser light beam during the crystallization to monitor the intensity of second harmonic generated light during crystallization.

The method of the present invention includes a rapid and extremely sensitive dynamic method for monitoring the crystallization of non-centrosymmetric phases of polymorphic materials. We have demonstrated that the method is rapid and sensitive enough to identify a phase transition in an energetic organic compound immediately prior to explosive decomposition. The invention can provide images of a non-crystalline polymorph in the presence of other polymorphs, which makes it useful for quality control applications such as for optimization processing conditions for crystallization. The procedure does not require a darkroom for the material, as opposed to Raman techniques that are usually performed with the sample in darkness. The invention also provides advantages over infrared techniques. While infrared spectral differences between crystalline polymorphs are often subtle, differences in SHG between centrosymmetric and non-centrosymmetric polymorphs can be much more easily detected.

The above examples of the present invention have been presented for purposes of illustration and description and are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for identifying and probing a phase transition in a polymorphic solid, comprising the steps of:

(a) interrogating a polymorphic solid with a laser beam at a chosen wavelength and frequency, the polymorphic solid selected from the group consisting of organic compounds, organic polymers, and mixtures thereof, the polymorphic solid being capable of existing in at least one non-centrosymmetric crystalline phase;

(b) inducing a phase transition in the solid; and (c) detecting the intensity of light scattered by the solid at a wavelength equal to one-half the wavelength of the interrogating laser beam.

2. The method of claim 1, wherein the polymorphic solid comprises a homogeneous solid.

3. The method of claim 1, wherein the polymorphic material comprises an explosive.

4. The method of claim 1, wherein the polymorphic solid comprises a polymorphic organic compound having pharmaceutical properties.

5. The method of claim 1, wherein the polymorphic solid comprises a heterogeneous solid.

* * * * *